United States Patent [19]

Maryanoff

[11] 4,136,097
[45] Jan. 23, 1979

[54] PROCESS AND PROMOTING AGENTS FOR THE PREPARATION OF LOWERALKYL 2-(N-R'-PYRRYL)-ALPHA-LOWERALKANOIC ACID ESTERS

[75] Inventor: Bruce E. Maryanoff, Levittown, Pa.
[73] Assignee: McNeil Laboratories, Inc., Fort Washington, Pa.
[21] Appl. No.: 785,004
[22] Filed: Apr. 6, 1977

Related U.S. Application Data

[63] Continuation-in-part of Ser. No. 716,405, Aug. 23, 1976, abandoned.

[51] Int. Cl.$^2$ .................................... C07D 207/32
[52] U.S. Cl. ........................ 260/326.2; 260/438.1
[58] Field of Search ............................ 260/326.2

[56] References Cited
U.S. PATENT DOCUMENTS

| | | | |
|---|---|---|---|
| 3,544,589 | 12/1970 | Orth et al. | 260/326.2 |
| 3,963,480 | 6/1976 | Bailey | 260/326.2 |

OTHER PUBLICATIONS

Rapoport et al., J. Org. Chem. vol. 14, pp. 664–669 (1949).
Berichte der Deutschen Chemischen Gesellschaft vol. 64, pp. 1924–1931 (1931).
Sohl et al.; J.A.C.S. vol. 55, pp. 3828–3833 (1933).
Maryanoff et al.; J. Het. Chem. vol. 14, pp. 177–178 (1977).
Leary et al.; Chemistry and Industry pp. 283–284 (1964).

*Primary Examiner*—Jose Tovar
*Assistant Examiner*—Mary Lee
*Attorney, Agent, or Firm*—Alice O. Robertson

[57] ABSTRACT

A process for the preparation of loweralkyl 2-(N-R'-pyrryl)-α- loweralkanoic acid esters in increased yield and/or isomeric purity, and copper (II) 1,3-diketonate, copper (II) salicylaldehyde, copper (II) monoamino-1,3-diketonate, and copper (II) salicylaldimine complexes useful as promoting agents for said process.

15 Claims, No Drawings

PROCESS AND PROMOTING AGENTS FOR THE PREPARATION OF LOWERALKYL 2-(N-R'-PYRRYL)-ALPHA-LOWERALKANOIC ACID ESTERS

REFERENCE TO RELATED APPLICATION

This application is a continuation-in-part of my co-pending application Ser. No. 716,405, filed August 23, 1976, now abandoned.

BACKGROUND OF THE INVENTION

This invention relates to a process for the preparation of loweralkyl 2-(N-R'-pyrryl)-α-loweralkanoic acid esters and more particularly for the preparation of loweralkyl 2-(N-methylpyrryl) acetic acid esters, and to promoting agents used in this process.

Loweralkyl 2-(N-R'-pyrryl)-α-loweralkanoic acid esters comprise a very useful class of compounds, being intermediates for the preparation of phenothiazine derivatives (see, for example, British Pat. No. 823,733 to F. P. Doyle and M. D. Mehta) and for the synthesis of the well-known anti-inflammatory agent tolmetin and its analogs (see, for example, U.S. Pat. No. 3,752,826), and are represented by the following generic formula:

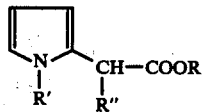

wherein R is loweralkyl, R' is a member selected from the group consisting of hydrogen and primary loweralkyl, and R" is a member selected from the group consisting of hydrogen and loweralkyl.

The prior art method for the preparation of compounds of this type is by the decomposition of a loweralkyl α-diazoloweralkanoate, formula (II), in the presence of an N-R'-pyrrole, formula (III), with copper bronze as a catalyst or promoting agent. See, for example, H. Rapoport and E. Jorgensen, J. Org. Chem., 14, 664(1949). The term "promoting agent" is used herein to mean a material which effectuates or facilitates a chemical reaction even when employed in a much less than stoichiometric amount (i.e., which functions as a catalyst, in the usual sense of the term, but which may be chemically altered in the course of the reaction). Given the chemical modification of the promoting agent, it necessarily differs from a true catalyst, which by definition remains unchanged by the reaction that it induces.

It has recently been discovered that this prior art preparative procedure does not yield only the desired 2-isomer but also yields some of the 3-isomer, formula (IV), as a by-product. This prior art process is illustrated by the following:

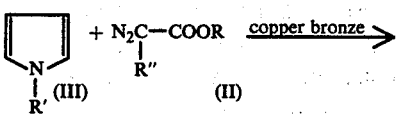

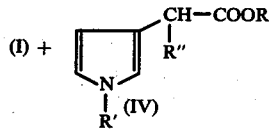

wherein R, R' and R" are as previously defined.

As these two isomers are practically inseparable, it is desired to have a process whereby one obtains a reaction product as enriched as possible in the desired 2-isomer (as "pure" as possible). As used herein, the term "pure" refers specifically to the degree of enrichment in the favored 2-isomer (i.e., to the relative amount of the desired 2-isomer compared to the undesired 3-isomer). The greater the ratio of 2-isomer to 3-isomer, the more "pure" the product mixture is said to be. Throughout the present application, this "purity" will be represented as the percent of the total amount of loweralkyl (N-R'-pyrryl)-α-loweralkanoic acid ester which is the desired 2-isomer.

It is also desirable to have a process which produces as much of the desirable 2-isomer as possible, regardless of the purity thereof. This characteristic will be referred to as the "yield" of the reaction and will be based upon the limiting reagent loweralkyl α-diazoloweralkanoate.

The prior art procedure is less than desirable in both the purity and the yield of the product. For example, the prior art preparative method for N-methylpyrrole acetic acid ethyl esters generally produces a product mixture having a purity of about 82% of the desired 2-isomer and a yield of the desired 2-isomer of about 32%, based on the ethyl diazoacetate. It should be noted at this point that, for this particular product, the literature often reports yields based upon N-methylpyrrole rather than ethyl diazoacetate; these yields appear considerably larger than those as calculated herein because they are not based upon the limiting reagent, ethyl diazoacetate. For valid comparision of two percentage yields, they must both be based on the same starting material. Throughout this application all yields are based on the amount of loweralkyl α-diazoloweralkanoate consumed in the reaction.

It is known in the chemical art that the effect of different types of catalysts on an individual reaction, or on related reactions, is very difficult to predict. A given catalyst may be ineffective in one reaction, while being the catalyst of choice in a closely related reaction. Different catalysts may result in different products or different ratios of products from the same starting materials. This unpredictability with respect to copper catalysts in diazo compound reactions is discussed, for example, on page 251 of "The Reaction of Diazoacetic Esters with Alkenes, Alkynes, Heterocyclic and Aromatic Compounds", Chapter 3, in *Organic Reactions*, 18, 217 (1970), by V. Dane and E. W. Warnhoff.

It has now surprisingly been discovered that the yield of the desired 2-isomer can be significantly increased and, in some case, the purity of the product improved through the use of the copper (II) 1,3-diketonate, copper (II) salicylaldehyde, copper (II) monoamino-1,3-diketonate, and copper (II) salicylaldimine complexes of the invention as promoting agents.

SUMMARY OF THE INVENTION

The present invention comprises a process for preparation of loweralkyl 2-(N-R'-pyrryl)-α-loweralkanoic acid esters in increased yield and/or isomeric purity by reacting an N-R'-pyrrole with a loweralkyl α-diazoloweralkanoate in the presence of a copper (II) complex of the invention described below. Certain of the copper (II) complexes are novel and constitute a further feature of the present invention.

A. COMPLEXES WITH DIOXO LIGANDS

The dioxo copper (II) salicylaldehyde and 1,3-diketonate complexes (promoting agents) of the invention may be represented by the following formula:

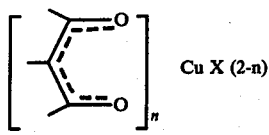

(V)

wherein "n" is the integer 1 or 2, X is a member selected from the group consisting of anions derived from monoprotic strong acids, such as for example, $-OSO_2CF_3$, picrate, hexafluorophosphate, nitrate, perchlorate, halide, loweralkylsulfonate, arenesulfonate, such as benzenesulfonate, toluenesulfonate, naphthalenesulfonate, and the like, fluoborate, trifluoroacetate, fluorosulfate, and the like; and oxy radicals, such as for example, loweralkoxy, phenoxy, and the like; and

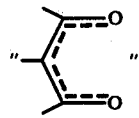

is intended to encompass all salicylaldehyde and 1,3-diketonate ligands capable of forming bidentate complexes with copper (II), whatever the substitution thereon. When n is 2, the two ligands may be the same or different.

It should be understood that certain 1,3-diketonate ligands are, because of their molecular geometry, incapable of forming bidentate complexes with copper (II). Examples of 1,3-diketones which are unsuitable for making the subject copper complexes are

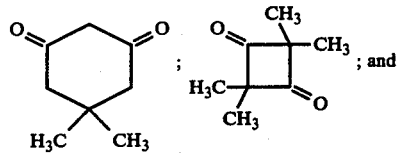

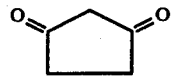

Because the keto groups on these compounds are directed away from each other due to the molecular geometry, these compounds cannot function as bidentate ligands.

The expression "1,3-diketonate" includes, for example, compounds of formula

wherein $R_1$ and $R_3$ are each members selected from the group consisting of loweralkyl, loweralkoxy, perfluoroloweralkyl, phenyl, 2-thienyl, β-naphthyl, and the like; and $R_2$ is a member selected from the group consisting of hydrogen and loweralkyl. Also included within the expression "1,3-diketonate" are the semicyclic 1,3-diketonates exemplified by the following:

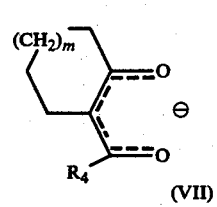

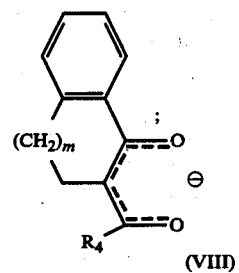

and

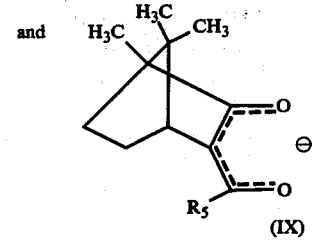

wherein $R_4$ is a member selected from the group consisting of loweralkyl, loweralkoxy, phenyl, and perfluoroloweralkyl; m is 0 or 1; and $R_5$ is a member selected from the group consisting of loweralkyl and perfluoroloweralkyl.

The expression "salicylaldehyde" includes, for example, compounds of formula

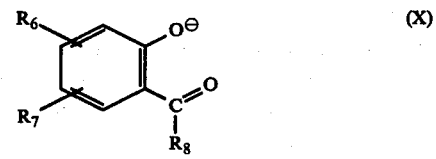

wherein $R_6$ and $R_7$ are each a member selected from the group consisting of hydrogen, halo, nitro, loweralkoxy, and loweralkyl; provided that $R_6$ and $R_7$ are oriented meta to each other if both are other than hydrogen; and $R_8$ is a member selected from the group consisting of hydrogen, loweralkyl, and perfluoroloweralkyl.

Also included within the expression "salicylaldehyde" is the bicyclic compound of formula:

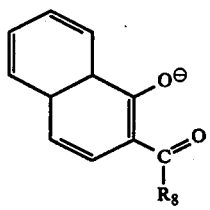
(Xa)

wherein R$_8$ is as previously defined.

As used herein, the terms "loweralkyl" and "loweralkoxy" mean straight or branched chain saturated aliphatic hydrocarbon radicals having from one to about six carbon atoms such as, for example, methyl, ethyl, isopropyl, pentyl, and the like loweralkyls, and methoxy, ethoxy, isopropoxy, pentoxy and the like loweralkoxys. The term "primary loweralkyl" means a loweralkyl in which the bonding carbon atom is unbranched such as, for example, methyl, ethyl, isobutyl, pentyl, and the like, but excluding, for example, isopropyl, sec-butyl, and the like. The term "perfluoroloweralkyl" means loweralkyl in which all hydrogen atoms have been replaced by fluoro such as, for example, trifluoromethyl, tetrafluoroethyl, and the like. the term "halo" includes fluoro, chloro, bromo, and iodo; and the term "halide" includes fluoride, chloride, bromide, and iodide.

The 1,3-diketones useful for preparation of the copper (II) 1,3-diketonate complexes of the invention are generally known or may be readily prepared according to the procedures described in Org. Syn., Coll. Vol. 3, 16, 17, 251 (1951) or C. R. Hauser, Org. Reactions, 8, 59 (1954). The salicylaldehyde useful for the preparation of the subject complexes are also generally known.

The preferred copper (II) 1,3-diketonate and copper (II) salicylaldehyde complexes (promoting agents) of the invention may be represented by the following formulas:

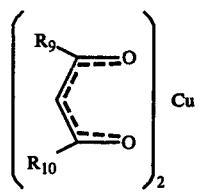
(XI)

wherein R$_9$ and R$_{10}$ are each members selected from the group consisting of loweralkyl, trifluoromethyl, phenyl, loweralkoxy, and 2-thienyl,

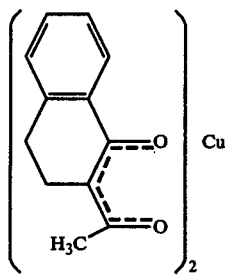
(XII)

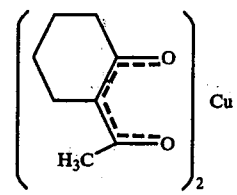
(XIII)

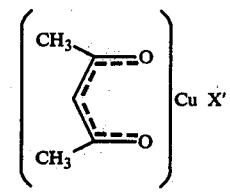
(XIV)

wherein X' is a member selected from the group consisting of OSO$_2$CF$_3$ and OCH$_3$; and

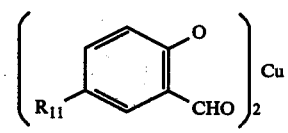
(XV)

wherein R$_{11}$ is a member selected from the group consisting of hydrogen, halo, nitro, and loweralkoxy.

Certain of the complexes of formula (XIV) are novel (e.g., those wherein X' is —OSO$_2$CF$_3$) and are considered to be part of the present invention. They may be prepared by metathesis of an appropriate complex of formula (X) with one equivalent of a suitable strong acid such as HOSO$_2$CF$_3$. The remaining dioxo complexes are generally known or may be readily prepared according to the procedures described by, for example, E. W. Berg and J. T. Truemper, J. Phys. Chem., 64, 487 (1960); J. H. Bertrand and R. L. Kaplan, Inorg. Chem., 4, 1657 (1965); or K. Clarke, J. Chem. Soc. 245 (1963). This latter reference teaches the preparation of the following complexes.

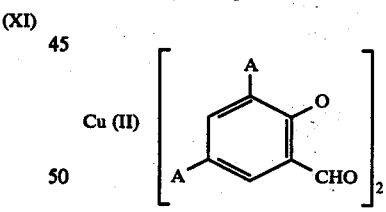

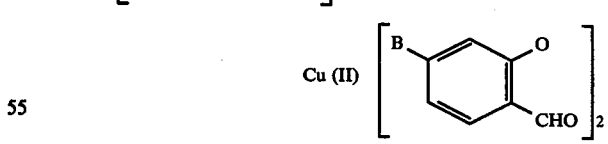

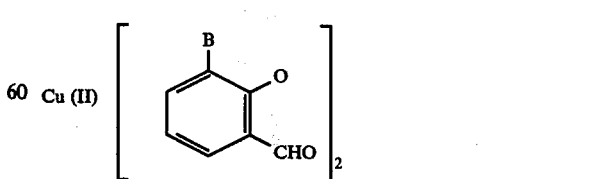

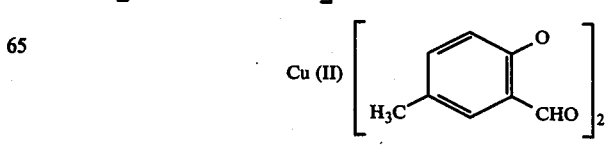

and

Cu (II) 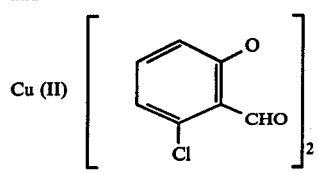

wherein A is a member selected from the group consisting of chloro, bromo, iodo, and nitro; and B is a member selected from the group consisting of methoxy, nitro, and chloro.

B. Complexes with oxoamino ligands

The oxoamino copper (II) complexes of the invention may be represented by the following formula:

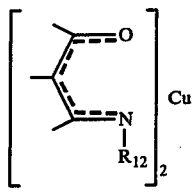 (XVI)

wherein

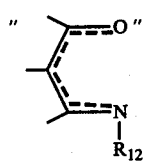

is intended to encompass all salicylaldimine and monoamino-1,3-diketonate ligands capable of forming bidentate complexes with copper (II), whatever the substitution thereon. The two ligands may be the same or different.

These oxoamino copper (II) salicylaldimine and copper (II) monoamino-1,3-diketonate complexes and the ligands from which they are made are generally known or may be readily prepared according to the procedures described by R. H. Holm, et al; Prog. in Inorg. Chem., 7, 83 (1966) and references contained therein. The ligands are conveniently prepared by reacting the appropriate corresponding dioxo ligand with an equivalent amount of the appropriate amine.

Preferred oxoamino copper (II) complexes of the invention may be represented by the following formula:

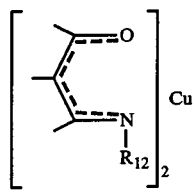 (XVI)

wherein $R_{12}$ is a member selected from the group consisting of hydrogen; loweralkyl; loweralkoxy; hydroxy; loweralkylamino; diloweralkylamino; phenyl; phenyl substituted with from one to three members each selected from the group consisting of loweralkyl, loweralkoxy, and halo; phenylloweralkyl; phenylloweralkyl in which said phenyl is substituted with from one to three members each selected from the group consisting of loweralkyl, loweralkoxy, and halo; phenylamino, and phenylamino in which said phenyl is substituted with from one to three members each selected from the group consisting of loweralkyl, loweralkoxy, and halo; provided that the $R_{12}$ groups on both oxoamino ligands taken together may be further selected from the group consisting of:

(a)

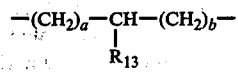

wherein a and b are integers such that a + b is from 1 to 6, and $R_{13}$ is a member selected from the group consisting of hydrogen, loweralkyl, phenyl and phenyl substituted with from one to three members each selected from the group consisting of loweralkyl, loweralkoxy, and halo;

(b)

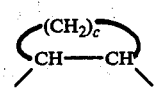

wherein c is an integer from 3 to 5;

(c) o-phenylene or o-phenylene substituted with from one to three members each selected from the group consisting of loweralkyl, loweralkoxy, and halo; and (d) $-(CH_2)_d-[NR_{14}-(CH_2)_e]_f-NR_{15}-(CH_2)_g-$, wherein d, e, and g are each 2 or 3, f is 0 or 1, and $R_{14}$ and $R_{15}$ are each selected from the group consisting of hydrogen and loweralkyl.

The complexes wherein both $R_{12}$ groups are taken together may be illustrated by the following, selected from class a) above:

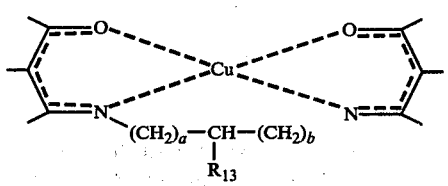 (XVII)

wherein a and b are as previously defined.

More preferred oxoamino copper (II) complexes of the invention may be represented by the following formulas:

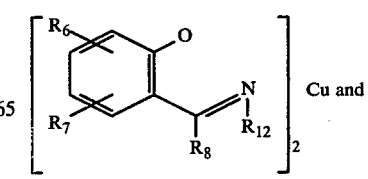 (XVIII)

(XIX)

-continued

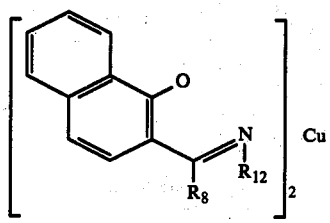

wherein: $R_6$, $R_7$, $R_8$, and $R_{12}$ are as previously defined.

Most preferred copper (II) salicylaldimine complexes (promoting agents) of the invention may be represented by the following formula:

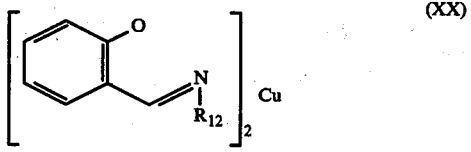

(XX)

wherein $R_{12}$ is a member selected from the group consisting of hydrogen; loweralkyl; phenyl; phenyl substituted with from one to three members each selected from the group consisting of loweralkyl, loweralkoxy, and halo; and phenylloweralkyl.

The copper (II) complexes of the invention may be used in place of the prior art copper bronze as a promoting agent for the preparation of loweralkyl 2-(N-R'-syrryl)-α-loweralkanoic acid esters by reacting an N-R'-syrrole with a loweralkyl α-diazololweralkanoate in the presence of one of said copper (II) complexes (promoting agents).

In one embodiment of the method of the present invention for preparation of 2-(N-R'-pyrryl)-α-loweralkanoic acid esters, the N-R'-pyrrole is present in excess, preferably about three equivalents for every equivalent of the loweralkyl α-diazololweralkanoate. The promoting agent is a member selected from the group consisting of compounds of formulas (V) and (XVI), and is present in about 0.1 to about 2 mol percent but preferably about 1 mol percent based on the loweralkyl α-diazololweralkanoate. The reaction may be conducted in the N-R'-pyrrole as solvent; a halogenated hydrocarbon, such as for example, methylene chloride, chloroform, bromoform, carbon tetrachloride, 1,2-dichloroethane, and the like; an aliphatic hydrocarbon, such as for example, cyclohexane, heptane, and the like; an aromatic hydrocarbon, such as for example, benzene, toluene, xylene, and the like; and the like. The preferred solvent is the N-R'-pyrrole itself, or a halogenated hydrocarbon, which is convenient for attainment of the required reaction temperature. The reaction mixture may be heated up to as high as 110° C., but a convenient operating temperature range is from about 30° to about 80° C. The preferred operating temperature depends upon the particular promoting agent used.

A small portion of the loweralkyl α-diazololweralkanoate is added initially for reasons of safety; i.e., to prevent an accumulation of the reagent which could result in the violent and sudden production of heat and nitrogen gas. Once nitrogen evolution has begun, the remainder of the loweralkyl α-diazololweralkanoate is added drop by drop maintaining a temperature sufficient for smooth and steady nitrogen evolution by warming or cooling as needed. Subsequent to addition of the loweralkyl α-diazololweralkanoate, the mixture may be heated to insure completion of the reaction, but this is frequently unnecessary.

The mixture of the desired 2-isomer and the undesired 3-isomer may be isolated by known techniques, for example by distillation.

A preferred process of the invention is that wherein the N-R'-pyrrole is N-methylpyrrole.

A more preferred process of the invention is that wherein the promoting agent is a member selected from the group consisting of compounds of formula (XI) wherein $R_9$ is methyl and $R_{10}$ is phenyl or $R_9$ and $R_{10}$ are both loweralkyl, a compound of formula (XII), a compound of formula (XIV) wherein X' is methoxy, and compounds of formula (XX) wherein $R_{12}$ is a member selected from the group consisting of hydrogen, isopropyl, p-chlorophenyl, and benzyl. These more preferred processes result in very high purity of the desired 2-isomer.

A second more preferred process of the invention is that wherein the promoting agent is a member selected from the group consisting of compounds of formula (XI) wherein $R_9$ is methyl and $R_{10}$ is perfluoroloweralkyl or $R_9$ and $R_{10}$ are both perfluoroloweralkyl, a compound of formula (XIV) wherein X' is $OSO_2CF_3$, and compounds of formula (XV) wherein $R_{11}$ is a member selected from the group consisting of chloro, hydrogen, and nitro. These more preferred processes result in a large increase in yield of the desired 2-isomer.

Better yield and generally better purity are obtained through use of the promoting agents and processes of the invention. The purity of the reaction mixture is as high as 93–94% in some cases and generally the same as or better than in the prior art, while the yield of the desired 2-isomer is increased by at least 10% and by as much as 50% over the yield in the prior art methods.

While preferred embodiments of the method of the invention have been set out above by way of illustration, it should be understood that the present invention encompasses any method for preparing loweralkyl 2-(N-R'-pyrryl)-α-loweralkanoic acid esters which comprises reacting N-R'-pyrrole and loweralkyl α-diazololweralkanoate in the presence of a copper (II) 1,3-diketonate, copper (II) salicylaldehyde, copper (II) monoamino-1,3-diketonate, or copper (II) salicylaldimine complex of the invention.

The present invention is further illustrated by the following examples:

EXAMPLE I

Ethyl 2-(N-methylpyrryl)acetate:

In a flask is placed 9.72 grams (120 mmol) N-methyl pyrrole and 158 mg (.016 mmole; 1.5 mol%) Cu(acetylacetonate)$_2$, abbreviated herein as "Cu(acac)$_2$". The mixture is heated to 50° C. after which a few drops of the 4.56 grams (40 mmol) ethyl diazoacetate are added with stirring. Nitrogen gas is evolved after about 1 minute and the mixture darkens, whereupon the remainder of the ethyl diazoacetate is added drop by drop over a period of 15 minutes. The reaction mixture is then heated and stirred for a further 45 minutes to insure completion of the reaction.

The excess and unreacted N-methylpyrrole is recovered by distillation of the product mixture in vacuo, after which the residue is flash distilled at a pot temperature of 80–100° C. (0.5 torr) to yield 2.40 grams of yellow liquid (36% yield based on ethyl diazoacetate) comprising 91% of the desired ethyl 2-(N-methylpyrryl) acetate.

EXAMPLE II

Ethyl 2-pyrrylacetate:

Following the procedure of Example I, but substituting an equivalent amount of pyrrole for the N-methylpyrrole used therein, resulted in 50% yield (based on ethyl diazoacetate) of the desired ethyl 2-pyrrylacetate in 94% purity. For comparison, the prior art process using copper bronze as the promoting agent resulted in only 38% yield (based on ethyl diazoacetate) of the desired ethyl 2-pyrrylacetate in 92% purity.

EXAMPLE III

The purity and yields of the desired 2-isomer ethyl 2-(N-methylpyrryyl)acetate obtained following the procedure of Example I but using equivalent amounts of illustrative catalysts of the invention for the $Cu(acac)_2$ used therein are shown in the following table, wherein Y and P stand for percentage yield and percentage purity, respectively:

| Formula | $R_9$ | $R_{10}$ | X' | $R_{11}$ | $R_{12}$ | Y | P |
|---|---|---|---|---|---|---|---|
| (XI) | $CH_3$ | phenyl | — | — | — | 37 | 90 |
| | $CH_3$ | $CF_3$ | — | — | — | 43 | 79 |
| | t-butyl | t-butyl | — | — | — | 36 | 89 |
| | $CF_3$ | $CF_3$ | — | — | — | 44 | 78 |
| | phenyl | phenyl | — | — | — | 37 | 87 |
| | $CH_3$ | $OC_2H_5$ | — | — | — | 41 | 84 |
| | 2-thienyl | $CF_3$ | — | — | — | 40 | 83 |
| (XII) | — | — | — | — | — | 40 | 89 |
| (XIII) | — | — | — | — | — | 39 | 86 |
| (XIV) | — | — | $OSO_2CF_3$ | — | — | 47 | 81 |
| | — | — | $OCH_3$ | — | — | 40 | 90 |
| (XV) | — | — | — | Cl | — | 48 | 80 |
| | — | — | — | H | — | 45 | 83 |
| | — | — | — | $NO_2$ | — | 47 | 75 |
| | — | — | — | $OCH_3$ | — | 42 | 83 |
| (XX) | — | — | — | — | H | 46 | 91 |
| | — | — | — | — | OH | 42 | 82 |
| | — | — | — | — | $CH(CH_3)_2$ | 47 | 94 |
| | — | — | — | — | benzyl | 44 | 94 |
| | — | — | — | — | $p\text{-}ClC_6H_4$ | 47 | 90 |
| | — | — | — | — | $-CH_2CH_2-$* | 37 | 89 |
| | — | — | — | — | $-(CH_2CH_2)_2NH$* | 37 | 89 |
| | — | — | — | — | $-(CH_2CH_2NHCH_2)_2$* | 38 | 89 |

*both $R_{12}$ groups taken together

EXAMPLE IV

Bis(5-chlorosalicylaldehyde) Copper(II):

To a solution of 1.61g of copper(II) nitrate trihydrate and 1.25g of sodium acetate in 25 ml of deionized water is added a warm solution of 2.08g of 5-chlorosalicylaldehyde in 25 ml of 95% ethanol. The mixture is stirred at 45°–50° C for 15 minutes, cooled, and filtered. The yellow-green solid which results, Bis(5-chlorosalicylaldehyde) copper(II), is rinsed with water and 95% ethanol and dried in vacuo.

EXAMPLE V

Following the procedure of Example IV, but substituting for the 5-chlorosalicylaldehyde used therein, an equivalent amount of the suitable starting material, there are prepared the following representative complexes:
Bis(benzoylacetonato) Copper(II);
Bis(2-acetyltetralonato) Copper(II);
Bis(2-acetylcyclohexanonato) Copper(II);
Bis(1,1,1,2,2,3,3,-heptafluoro-7,7-dimethyloctane-4,6-dionato) Copper (II);
Bis(3-trifluoroacetylcamphorato) Copper(II);
Bis(2,4-heptanedionato) Copper (II);
Bis(1,1,1-trifluoropentane-2,4-dionato) Copper(II);
Bis[1,1,1,5,5,5-hexafluoropentane-2,4-dionato] Copper-(II);
Bis(3-methylpentane-2,4-dionato) Copper(II);
Bis(ethylacetoacetato) Copper(II);
Bis(3-pivaloyl comphorato) Copper(II);
Bis(2-furoylacetonato) Copper(II); and Bis(dibenzoylmethanato) Copper(II).

EXAMPLE VI (Acetylacetonato) Copper(II) trifluoromethylsulfonate:

A suspension of 262 mg. (1 mmole) of $Cu(acac)_2$ in 3 ml of dichloromethane is treated dropwise with stirring with 150 mg (1 mmole) of trifluoromethyl sulfonic acid. The resulting green solution is decanted from a small amount of residual solid and diluted with hexane, whereupon a green precipitate, (acetylacetonato) Copper(II) trifluoromethylsulfonate, results, m.p. 182° C.

EXAMPLE VII

Following the procedure of Example VI. but substituting for the $Cu(acac)_2$ and the trifluoromethylsulfonic acid used therein, the equivalent amount of suitable starting materials, there are prepared the following complexes:
(Acetylacetonato) Copper (II) trifluoroacetate;
(Benzoylacetonato) Copper (II) fluorosulfate;
(Acetylacetonato) Copper (II) picrate;
(Acetylacetonato) Copper (II) hexafluorophosphate;
(Acetylacetonato) Copper (II) nitrate;
(Acetylacetonato) Copper (II) perchlorate;
(Acetylacetonato) Copper (II) chloride;
(Acetylacetonato) Copper (II) ethylsulfonate;
(Acetylacetonato) Copper (II) benzenesulfonate;
(Acetylacetonato) Copper (II) fluoborate.

EXAMPLE VIII

Bis-(β-salicylaldiminoethyl)amine Copper(II):

To a solution of 2.44g (20 mmol) of salicylaldehyde in 20 ml of absolute ethanol was added 1.03g (10 mmol) of diethylenetriamine and the whole was allowed to stand at ambient temperature for one hour. A solution of Copper (II) acetate (from 2.42g of $Cu(No_3)_2\cdot 3H_2O$ and 1.7g of sodium acetate) in 20 ml of deionized water was added, and the whole was allowed to stand for 18 hours.

The resulting purple crystals were collected by filtration, washed with 75% aqueous ethanol, and dried in vacuo at 70° to yield Bis-(β-salicylaldiminoethyl)amine Copper(II); m.p. ca. 240° C (dec).

EXAMPLE IX

Following the procedure of Example VIII, but substituting an equivalent amount of triethylenetetramine for the diethylenetriamine used therein, there is prepared:

1,2-Bis(β-salicylaldiminoethylamino)ethane Copper-(II); m.p. ca. 240° C (dec).

EXAMPLE X

Following the procedure of Example I, but substituting for the N-methylpyrrole and ethyl diazoacetate used therein equivalent amounts of the appropriate starting materials, the following 2-pyrrylacetic acid esters are produced in increased yield or yield and purity over the prior art process:
Methyl 2-(N-methylpyrryl)acetate;
Methyl 2-(N-ethylpyrryl)acetate;
Ethyl 2-(N-ethylpyrryl)acetate;
n-Propyl 2-(N-methylpyrryl)acetate;
Isopropyl 2-(N-methylpyrryl)acetate;
Methyl 2-(N-methylpyrryl)-α-propionate;
Butyl 2-(N-ethylpyrryl)-α-propionate;
Ethyl 2-(N-n-propylpyrryl)-α-isovalerate; and
Methyl 2-(N-isobutylpyrryl)-α-acetate.

EXAMPLE XI

Bis(Salicylaldimino) Copper (II):

Following the procedure of S. V. Sheat and T. N. Waters, *Inorg. Nucl. Chem.*, 26, 1221 (1965), 500 mg of bis-(salicylaldehyde) copper (II) was combined with 5 ml of 10% ammonium hydroxide and the mixture was stirred vigorously for one hour. The solid was filtered off and dried in air, affording 410 mg of pale green powder identified by its ultraviolet spectrum as bis(-salicylaldimino) copper (II).

EXAMPLE XII

Bis(N-isopropylsalicylaldimino) Copper (II):

Following the procedures of L. Sacconi et al, J. Chem. Soc., 1964, 274, 1.22g of salicylaldehyde (10 mmol) in 10 ml of absolute ethanol was treated with 590 mg of isopropylamine (10 mmol) at ca. 15°. The reaction was stoppered to prevent loss of the volatile amine and allowed to stand for one hour. A solution of 1.21g of Cu (NO₃)₂·3H₂O and 0.85g of sodium acetate in 10 ml of deionized water was added with stirring. Filtration afforded bis(N-isopropylsalicylaldimino) copper (II) as a brown solid (air-dried); m.p. 140–143°.

EXAMPLE XIII

Following the procedure of Example XII, but substituting equivalent amounts of the appropriate salicylaldehyde or 1,3-diketone and amine or hydrazine for the salicylaldehyde and isopropylamine used therein, the following are prepared:
Bis(N-hydroxysalicylaldimino) Copper (II);
Bis(N-benzylsalicylaldimino) Copper (II);
Bis[N-(p-chlorophenyl)salicylaldimino Copper (II);
Bis[N-(n-hexyl)salicylaldimino] Copper (II);
Bis[N-(p-tolyl)salicylaldimino] Copper (II);
Bis[N-(p-chlorobenzyl)salicylaldimino] Copper (II);
Bis[N-methoxysalicylaldimino] Copper (II);
Bis[N-methylaminosalicylaldimino] Copper (II);
Bis[N-(dimethylamino)salicylaldimino] Copper (II)
Bis[N-(phenylamino)salicylaldimino] Copper (II);
Bis[N-(p-chlorophenylamino)salicylaldimino] Copper (II);

the above Examples have been provided by way of illustration and not to limit the scope of the present invention, which scope is defined by the following claims.

What is claimed is:

1. A method for preparing a loweralkyl 2-(N-R'-pyrryl)-α-loweralkanoic acid ester of the formula

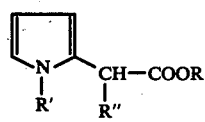

wherein R is loweralkyl; R' is selected from the group consisting of hydrogen and primary lower alkyl; R" is selected from the group consisting of hydrogen and lower alkyl; which comprises reacting an N-R'-pyrrole of the formula

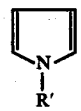

wherein R' is as above defined with a loweralkyl α-diazoloweralkanoate of the formula

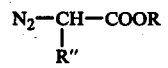

wherein R and R" are as above defined in the presence of a copper (II) complex selected from those of formula

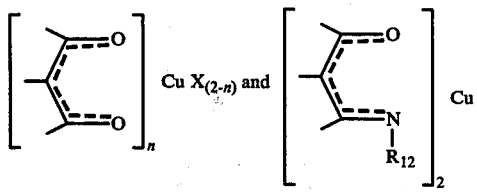

wherein:
n is an integer of from 1 to 2;
X is selected from the group consisting of anions of monprotic strong acids, lower alkoxy radicals and a phenoxy radical;

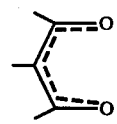

is a 1,3-diketonate or a salicylaldehyde ligand capable of forming bidentate complexes with copper (II) selected from the group consisting of (a) compounds of formula

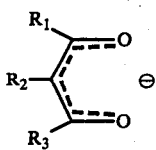

wherein $R_1$ and $R_3$ are each selected from the group consisting of loweralkyl, loweralkoxy, perfluoroloweralkyl, phenyl, 2-thienyl and β-naphthyl; and $R_2$ is selected from the group consisting of hydrogen and loweralkyl; (b) compounds of formula

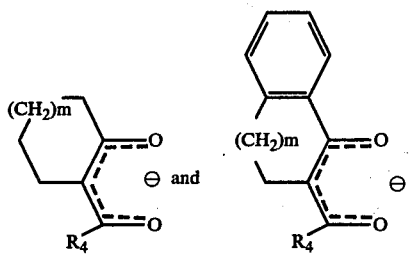

wherein $R_4$ is selected from the group consisting of loweralkyl, loweralkoxy, phenyl, and perfluoroloweralkyl; and m is 0 or 1; (c) compounds of formula

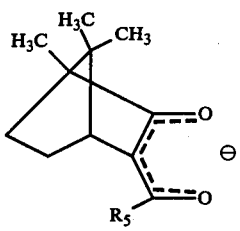

wherein $R_5$ is selected from the group consisting of loweralkyl and perfluoroloweralkyl; and (d) compounds of formula

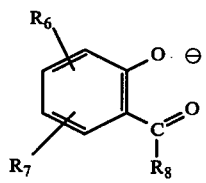

and wherein $R_6$ and $R_7$ are each selected from the group consisting of hydrogen, halo, nitro, loweralkoxy and loweralkyl; provided that said $R_6$ and $R_7$ are oriented meta to each other if both are other than hydrogen; and $R_8$ is selected from the group consisting of hydrogen, loweralkyl, and perfluoroloweralkyl; and

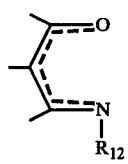

is a monoamino-1,3-diketonate or salicylaldimine ligand capable of forming bidentate complexes with copper (II) selected from the group consisting of

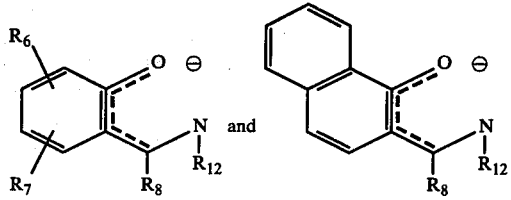

wherein $R_6$, $R_7$ and $R_8$ are as defined above and $R_{12}$ is selected from the group consisting of hydrogen; loweralkyl; loweralkoxy; hydroxy; loweralkylamino; diloweralkylamino; phenyl substituted with from one to three members each selected from the group consisting of loweralkyl, loweralkoxy, and halo; phenylloweralkyl; phenylloweralkyl in which said phenyl is substituted with from one to three members each selected from the group consisting of loweralkyl, loweralkoxy, and halo; phenylamino, and phenylamino in which said phenyl is substituted with from one to three members each selected from the group consisting of loweralkyl, loweralkoxy, and halo; provided that the $R_{12}$ groups on both ligands taken together may be further selected from the group consisting of

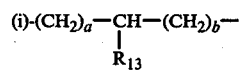

wherein a and b integers such that a + b is from 1 to 6, and $R_{13}$ is selected from the group consisting of hydrogen, loweralkyl, phenyl, and phenyl substituted with from one to three members each selected from the group consisting of loweralkyl, loweralkoxy, and halo;

wherein c is an integer from 3 to 5; (iii) o-phenylene or o-phenylene substituted with from one to three members each selected from the group consisting of loweralkyl, loweralkoxy, and halo; and (iv) —(CH$_2$)$_d$—[NR$_{14}$—(CH$_2$)$_e$]$_f$—NR$_{15}$—(CH$_2$)$_g$—, wherein d, e, and g are each 2 or 3, f is 0 or 1, and $R_{14}$ and $R_{15}$ are each selected from the group consisting of hydrogen and loweralkyl.

2. A method for preparing a loweralkyl 2-(N-methylpyrryl)-α-loweralkanoic acid ester having the formula

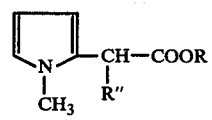

wherein R is loweralkyl and R″ is selected from the group consisting of hydrogen and loweralkyl; which comprises reacting N-methylpyrrole with a loweralkyl α-diazoloweralkanoate represented by the formula

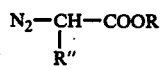

wherein R and R" are as above identified in the presence of a copper (II) complex selected from the group consisting of

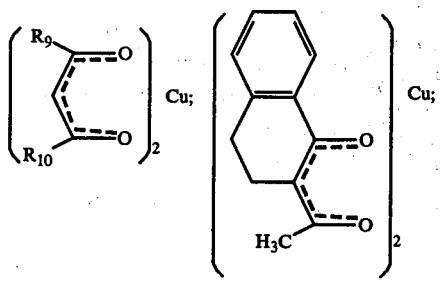

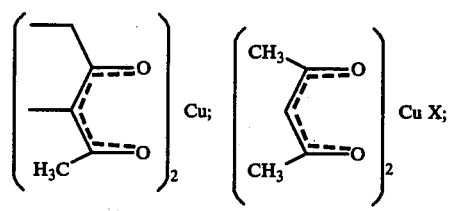

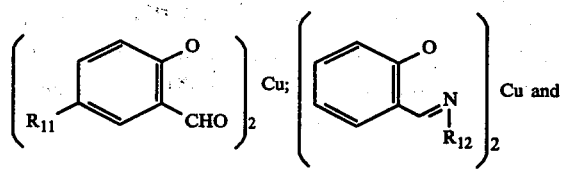

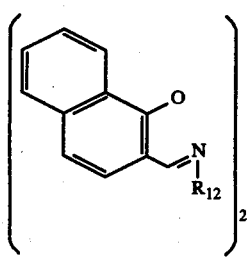

wherein $R_9$ and $R_{10}$ are each selected from the group consisting of loweralkyl, perfluoroloweralkyl, phenyl, loweralkoxy, and 2-thienyl; X is selected from the group consisting of $OSO_2CF_3$ and $OCH_3$; $R_{11}$ is selected from the group consisting of hydrogen, halo, nitro and loweralkoxy; and $R_{12}$ is selected from the group consisting of hydrogen, loweralkyl, phenyl, phenyl substituted with from one to three members each selected from the group consisting of loweralkyl, loweralkoxy, and halo; and phenylloweralkyl.

3. A method for preparing in increased purity and in increased yield, a lower alkyl 2-(N-R'-pyrryl)-α-loweralkanoic acid ester of the formula

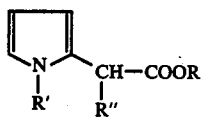

wherein R is lower alkyl; R' is selected from the group consisting of hydrogen and primary lower alkyl; R" is selected from the group consisting of hydrogen and lower alkyl; which comprises adding portionwise while maintaining smooth nitrogen evolution, a lower alkyl α-diazo-lower-alkanoate of the formula

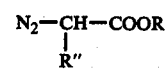

wherein R and R" are as above defined, to a mixture of an N-R'-pyrrole of the formula

wherein R' is as above defined and a copper(II) complex wherein (a) for preparing said lower alkyl 2-(N-R'-pyrryl)-α-lower-alkanoic acid acid ester in increased purity, said copper(II) complex is selected from those of the formulas

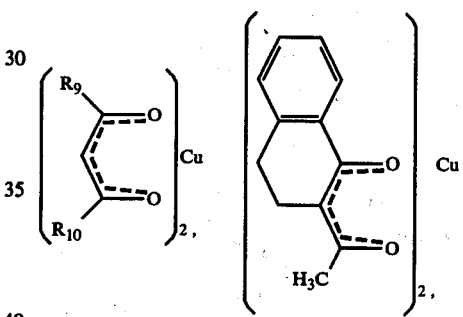

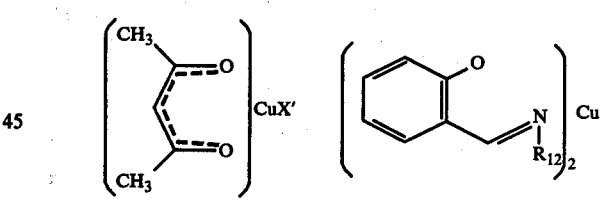

wherein $R_9$ and $R_{10}$ are methyl and phenyl, respectively, or are both lower alkyl, and $R_{12}$ is selected from the group consisting of hydrogen, isopropyl, p-chloro-phenyl and benzyl, and X' is methoxy; or (b) for preparing said lower alkyl 2-(N-R'-pyrryl)-α-lower-alkanoic acid ester in increased yield, said copper(II) complex is selected from those of the formulas

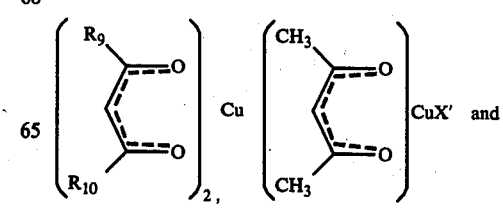

-continued

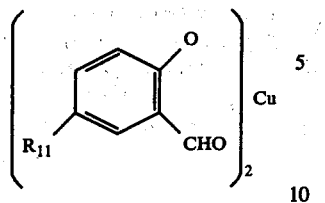

wherein $R_9$ and $R_{10}$ are methyl and perfluoro-lower-alkyl, respectively, or are both perfluoro-lower-alkyl, $R_{11}$ is selected from the group consisting of hydrogen, chloro and nitro, and X' is —OSO$_2$CF$_3$.

4. A method according to claim 3 for preparing the lower alkyl 2-(N-R'-pyrryl)-α-lower-alkanoic acid ester in increased purity wherein the copper(II) complex is selected from those of the formulas

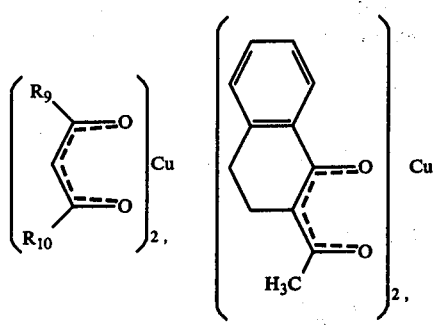

wherein $R_9$ and $R_{10}$ are methyl and phenyl, respectively, or are both lower alkyl, and $R_{12}$ is selected from the group consisting of hydrogen, isopropyl, p-chlorophenyl and benzyl, and X' is methoxy.

5. A method according to claim 3 for preparing the lower 2-(N-R'-pyrryl)-α-lower-alkanoic acid ester in increased yield wherein the copper(II) complex is selected from those of the formulas

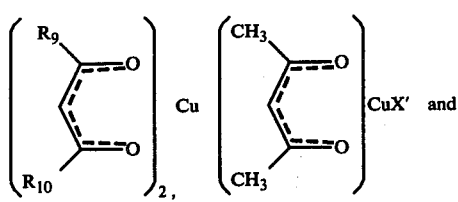

-continued

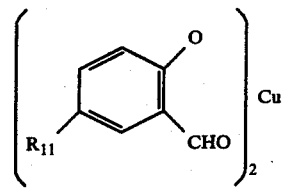

wherein $R_9$ and $R_{10}$ are methyl and perfluoro-lower-alkyl, respectively, or are both perfluoro-lower-alkyl, $R_{11}$ is selected from the group consisting of hydrogen, chloro and nitro, and X' is OSO$_2$CF$_3$.

6. The method of claim 2 wherein the copper (II) complex is:

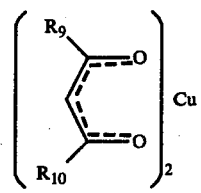

wherein $R_9$ and $R_{10}$ are each members selected from the group consisting of loweralkyl, perfluoroloweralkyl, phenyl, loweralkoxy and 2-thienyl.

7. The method of claim 2, wherein the copper (II) complex is

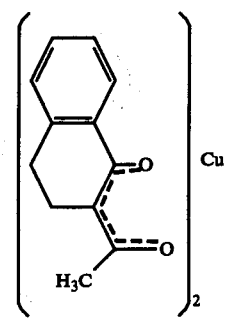

8. The method of claim 2, wherein the copper (II) complex is

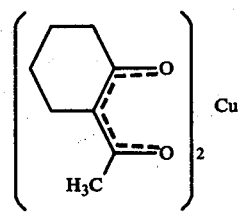

9. The method of claim 2, wherein the copper (II) complex is

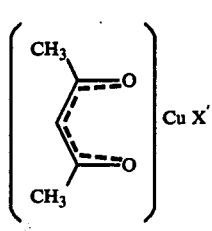

wherein X' is a member selected from the group consisting of $OSO_2CF_3$ and $OCH_3$.

10. The method of claim 2, wherein the copper (II) complex is

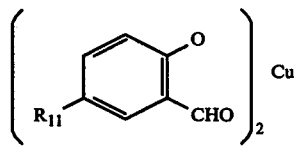

wherein $R_{11}$ is a member selected from the group consisting of hydrogen, halo, nitro and loweralkoxy.

11. The method of claim 2, wherein the copper (II) complex is a member selected from the group consisting of

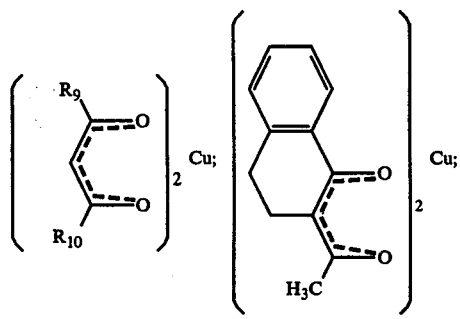

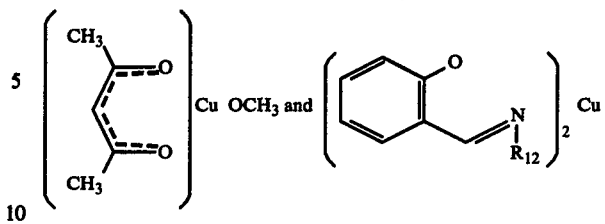

wherein $R_9$ is methyl and $R_{10}$ is phenyl or $R_9$ and $R_{10}$ are both t-butyl; and $R_{12}$ is a member selected from the group consisting of hydrogen, isopropyl, p-chlorophenyl, and benzyl.

12. The method of claim 2 wherein the copper (II) complex is a member selected from the group consisting of:

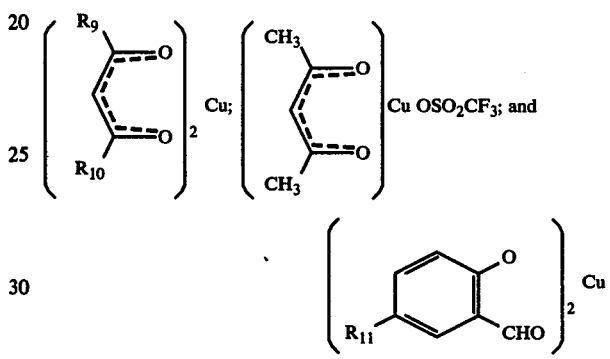

wherein $R_9$ is methyl or trifluoromethyl, $R_{10}$ is trifluoromethyl, and $R_{11}$ is a member selected from the group consisting of chloro, nitro, and hydrogen.

13. The method of claim 2 wherein the N-methyl-pyrrole is present in excess, based on the loweralkyl α-diazoloweralkanoate.

14. The method of claim 2 wherein the copper (II) complex is present in about 1 mol percent of the amount of loweralkyl α-diazoloweralkanoate.

15. The method of claim 2 wherein the reaction mixture is heated to a temperature from about 30° to about 80° C. during the reaction.

* * * * *

UNITED STATES PATENT AND TRADEMARK OFFICE
CERTIFICATE OF CORRECTION

PATENT NO. : 4,136,097
DATED : January 23, 1979
INVENTOR(S) : Bruce E. Maryanoff It is certified that error appears in the above-identified patent and that said Letters Patent are hereby corrected as shown below:

At Column 1, Line 46, "E. jorgensen" should be
    -- E. Jorgensen --.
At Column 2, Line 60, "case" should be -- cases --.
At Column 9, Lines 31-32, "syrryl" should be -- pyrryl --.
At Column 9, Line 33, "syrrole" should be -- pyrrole --.
At Column 11, Example III, in the table, Line 38,

| $R_{12}$ | Y | P |
|---|---|---|
| "CH(CH$_3$)$_2$ | 47 | 94" | should be

| $R_{12}$ | Y | P |
|---|---|---|
| -- CH(CH$_3$)$_2$ | 47 | 94 --. |

At Column 17, Lines 21-28, in the formula,

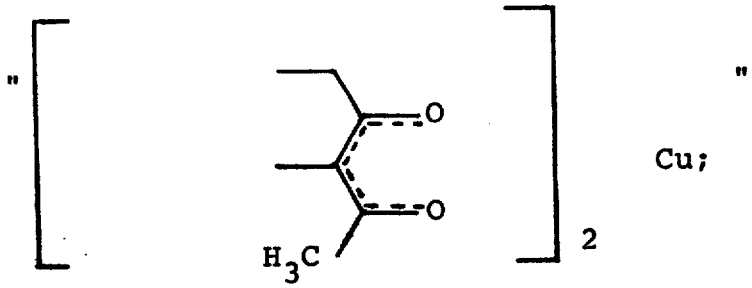

Cu;

UNITED STATES PATENT AND TRADEMARK OFFICE
CERTIFICATE OF CORRECTION

PATENT NO. : 4,136,097

DATED : January 23, 1979

INVENTOR(S) : Bruce E. Maryanoff

It is certified that error appears in the above-identified patent and that said Letters Patent are hereby corrected as shown below:

should be

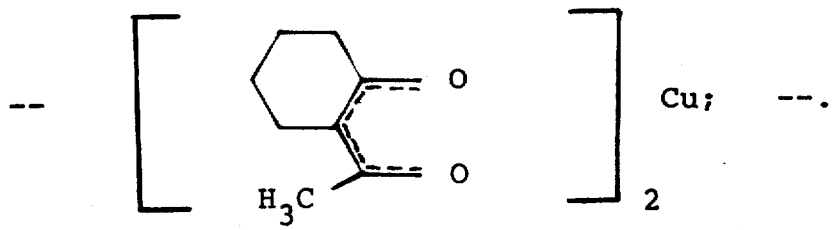

Signed and Sealed this

Twelfth Day of June 1979

[SEAL]

Attest:

RUTH C. MASON
Attesting Officer

DONALD W. BANNER
Commissioner of Patents and Trademarks